(12) United States Patent
Takahashi et al.

(10) Patent No.: US 9,726,614 B2
(45) Date of Patent: Aug. 8, 2017

(54) ANALYSIS APPARATUS

(71) Applicant: PANASONIC CORPORATION, Osaka (JP)

(72) Inventors: Tatsuya Takahashi, Shiga (JP); Tomoya Kusakabe, Shiga (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 53 days.

(21) Appl. No.: 14/423,996

(22) PCT Filed: Jul. 31, 2013

(86) PCT No.: PCT/JP2013/004638
§ 371 (c)(1),
(2) Date: Feb. 25, 2015

(87) PCT Pub. No.: WO2014/045509
PCT Pub. Date: Mar. 27, 2014

(65) Prior Publication Data
US 2015/0253254 A1 Sep. 10, 2015

(30) Foreign Application Priority Data

Sep. 21, 2012 (JP) .................................. 2012-208068

(51) Int. Cl.
*G01N 21/84* (2006.01)
*G01N 33/02* (2006.01)
(Continued)

(52) U.S. Cl.
CPC ............ *G01N 21/84* (2013.01); *G01J 3/0205* (2013.01); *G01N 21/359* (2013.01);
(Continued)

(58) Field of Classification Search
CPC ...... G01N 21/84; G01N 33/02; G01N 21/359; G01N 21/3563; G01N 2201/061;
(Continued)

(56) References Cited

U.S. PATENT DOCUMENTS

| | | | | | |
|---|---|---|---|---|---|
| 4,649,281 | A | * | 3/1987 | Schmitt | B01D 17/0214 137/172 |
| 5,313,941 | A | * | 5/1994 | Braig | A61B 5/14532 356/41 |

(Continued)

FOREIGN PATENT DOCUMENTS

| | | |
|---|---|---|
| JP | H05-118984 A | 5/1993 |
| JP | H07-260680 A | 10/1995 |

(Continued)

OTHER PUBLICATIONS

International Search Report issued in International Application No. PCT/JP2011/004638 dated Oct. 15, 2013, with English translation.

(Continued)

*Primary Examiner* — Tarifur Chowdhury
*Assistant Examiner* — Mohamed K Amara
(74) *Attorney, Agent, or Firm* — McDermott Will & Emery LLP

(57) ABSTRACT

An analysis apparatus is provided with: a light emitting part, a light dispersing part, a light detecting part, a storage unit, and a control unit. The light dispersing part disperses first reflected light reflected from a food product when the food product has been irradiated with light from the light emitting part. The light detecting part: generates first detection data by detecting the first reflected light dispersed; and, when a food product sample containing known ingredients is irradiated with light from the light emitting part, generates second detection data by detecting second reflected light reflected from the food product sample and dispersed by the (Continued)

light dispersing part. The storage unit stores a regression formula computed using the second detection data as a parameter. The control unit estimates the ingredients contained in the food product using the first detection data and the regression formula stored in the storage unit.

6 Claims, 3 Drawing Sheets

(51) Int. Cl.
*G01N 21/3563* (2014.01)
*G01N 21/359* (2014.01)
*G01J 3/02* (2006.01)
*G01J 3/12* (2006.01)

(52) U.S. Cl.
CPC .......... *G01N 21/3563* (2013.01); *G01N 33/02* (2013.01); *G01J 2003/1217* (2013.01); *G01N 2201/061* (2013.01)

(58) Field of Classification Search
CPC .......... G01N 21/474; G01N 2021/4735; G01N 2021/4742; G01N 2021/4759; G01N 2201/0221; G01N 21/255; G01N 21/31; G01N 2021/3166; G01N 2021/3177; G01N 21/274; G01N 21/35; G01N 21/3577; G01J 3/0205; G01J 2003/1217; G01J 3/02; G01J 3/10; G01J 3/18; G01J 3/36; G01J 3/42; G01J 1/32; G01J 3/021; G01J 3/0272; G02B 5/1809; G02B 5/203; G02B 5/201; G02B 26/02
See application file for complete search history.

(56) References Cited

U.S. PATENT DOCUMENTS

| | | | | |
|---|---|---|---|---|
| 5,494,032 | A * | 2/1996 | Robinson | A61B 5/14542 356/41 |
| 6,587,575 | B1 * | 7/2003 | Windham | G01N 21/31 250/458.1 |
| 6,624,888 | B2 * | 9/2003 | Panigrahi | A01D 33/00 356/326 |
| 6,654,125 | B2 * | 11/2003 | Maynard | G01J 3/453 356/451 |
| 9,297,770 | B2 * | 3/2016 | Tralshawala | G01N 33/02 |
| 9,310,299 | B2 * | 4/2016 | Lai | G01N 21/253 |
| 2002/0185608 | A1 | 12/2002 | Wieser | |
| 2003/0191398 | A1 * | 10/2003 | Motz | A61B 5/0075 600/478 |
| 2005/0231723 | A1 * | 10/2005 | Blasenheim | B01L 3/5027 356/414 |
| 2005/0232822 | A1 * | 10/2005 | Reed | G01N 35/028 422/552 |
| 2007/0218174 | A1 * | 9/2007 | Hanamatsu | G01G 19/4146 426/231 |
| 2009/0292186 | A1 * | 11/2009 | Xu | A61B 5/14532 600/316 |
| 2011/0168895 | A1 * | 7/2011 | Nagai | G01J 3/02 250/338.4 |
| 2012/0035442 | A1 * | 2/2012 | Barman | A61B 5/14532 600/316 |
| 2013/0003054 | A1 * | 1/2013 | Kamimura | G01J 3/02 356/300 |
| 2013/0010294 | A1 * | 1/2013 | Matsuda | G01N 21/3563 356/326 |
| 2013/0066172 | A1 * | 3/2013 | Kulcke | A61B 5/14532 600/310 |

FOREIGN PATENT DOCUMENTS

| | | |
|---|---|---|
| JP | 2003-065955 A | 3/2003 |
| JP | 2005-017210 A | 1/2005 |
| JP | 2005-292128 A | 10/2005 |
| JP | 2008-175760 A | 7/2008 |
| JP | 2009-098015 A | 5/2009 |
| JP | 2009-103480 A | 5/2009 |
| JP | 2011-202971 A | 10/2011 |
| JP | 2011-203085 A | 10/2011 |
| WO | 2012/005350 A1 | 1/2012 |

OTHER PUBLICATIONS

International Preliminary Report on Patentability dated Mar. 24, 2015 issued in International Patent Application No. PCT/JP2013/004638.
Japanese Office Action dated Nov. 15, 2016 issued in Japanese Patent Application No. 2012-208068 (with English translation).
Japanese Office Action dated May 9, 2017 issued in Japanese Patent Application No. 2012-208068 (with English translation).

* cited by examiner

ANALYSIS APPARATUS

RELATED APPLICATIONS

This application is the U.S. National Phase under 35 U.S.C. §371 of International Application No. PCT/JP2013/004638, filed on Jul. 31, 2013, which in turn claims the benefit of Japanese Application No. 2012-208068, filed on Sep. 21, 2012, the disclosures of which are incorporated by reference herein.

TECHNICAL FIELD

The present invention relates to an analysis apparatus that analyzes, for example, components or calories of food.

BACKGROUND ART

When conducting a non-destructive test using the optical properties of an analyzed subject, known processes generally use light having a wavelength in a near-infrared region or the like. A known process for measuring calories of food particularly uses the near-infrared light (e.g., patent document 1).

Such a process for measuring calories obtains the known calories, which are acquired by chemically analyzing samples of various food examples, and the near-infrared wavelength of calories of the various food samples acquired from a multiple regression analysis of the absorbance of each sample. The calories of a food that is the measured subject are estimated using the near-infrared wavelength.

PRIOR ART DOCUMENT

Patent Document

Patent Document 1: Japanese Laid-Open Patent Publication No. 2005-292128

SUMMARY OF THE INVENTION

Problems that are to be Solved by the Invention

In such a process for measuring calories that is described above, a pre-processing spectroscopic technique is used to measure a near-infrared absorption spectrum that plots absorbance relative to wavelengths. Such measurement is time-consuming. Additionally, a spectral unit, such as a light chopper, is firstly necessary to disperse light into a plurality of single near-infrared wavelengths that are attributed to calories and each nutritional component of food. This results in an enlargement of an apparatus.

The present invention focuses on such problems. It is an object of the present invention to provide an analysis apparatus that briefly and easily analyzes a component contained in an analyzed subject or calories of an analyzed subject without enlarging the analysis apparatus.

Means for Solving the Problem

To solve the problem, one aspect of an analysis apparatus is capable of analyzing a component contained in an analyzed subject or calories of the analyzed subject. The analysis apparatus includes a light emitter that emits light. A spectral unit disperses first reflection light reflected from the analyzed subject or first transmission light transmitted through the analyzed subject when the light emitter irradiates the analyzed subject with light. A light detector detects the first reflection light or the first transmission light dispersed by the spectral unit and generates first detection data. When the light emitter irradiates an analysis sample with light, in which the analysis sample includes a known component or has known calories, the light detector detects second reflection light, which is reflected from the analysis sample and dispersed by the spectral unit, or second transmission light, which is transmitted through the analysis sample and is dispersed by the spectral unit, and generates second detection data. A memory stores a regression equation calculated using the second detection data as a parameter. An analyzer estimates the component contained in the analyzed subject or the calories of the analyzed subject using the first detection data and the regression equation stored in the memory.

Preferably, the above configuration further includes a temperature meter capable of measuring temperature of the analyzed subject. The analyzer corrects the component contained in the analyzed subject or the calories of the analyzed subject based on the temperature of the analyzed subject measured by the temperature meter.

Preferably, the above configuration further includes a weight meter capable of measuring weight of the analyzed subject. The regression equation stored in the memory is calculated using the second detection data and the weight of the analysis sample measured by the weight meter as parameters. The analyzer estimates weight of the component contained in the analyzed subject using the first detection data, the weight of the analyzed subject measured by the weight meter, and the regression equation.

Preferably, the above configuration further includes a light transmissive plate on which the analyzed subject is placed. The light emitter, the spectral unit, and the light detector are located below the plate. The light emitter irradiates the analyzed subject placed on the plate with light passing through the plate. The spectral unit disperses first reflection light reflected from the analyzed subject through the plate. The light detector detects the first reflection light dispersed by the spectral unit.

Preferably, in the above configuration, the analyzed subject is food, and the component is at least one of protein, fat, and carbohydrate.

Preferably, in the above configuration, the spectral unit includes a plurality of optical filters, each of the optical filters allows transmission of light having a specified wavelength and restricts transmission of light having wavelengths other than the specified wavelength, the light detector includes a plurality of light reception elements, and each of the light reception elements (18a) receives light transmitted through a corresponding one of the optical filters.

Effects of the Invention

According to the present invention, a component contained in an analyzed subject or calories of an analyzed subject can be analyzed in a brief and easy manner without enlarging an apparatus.

EMBODIMENTS OF THE INVENTION

One embodiment of an analysis apparatus according to the present invention will now be described with reference to the drawings.

Figure 1:
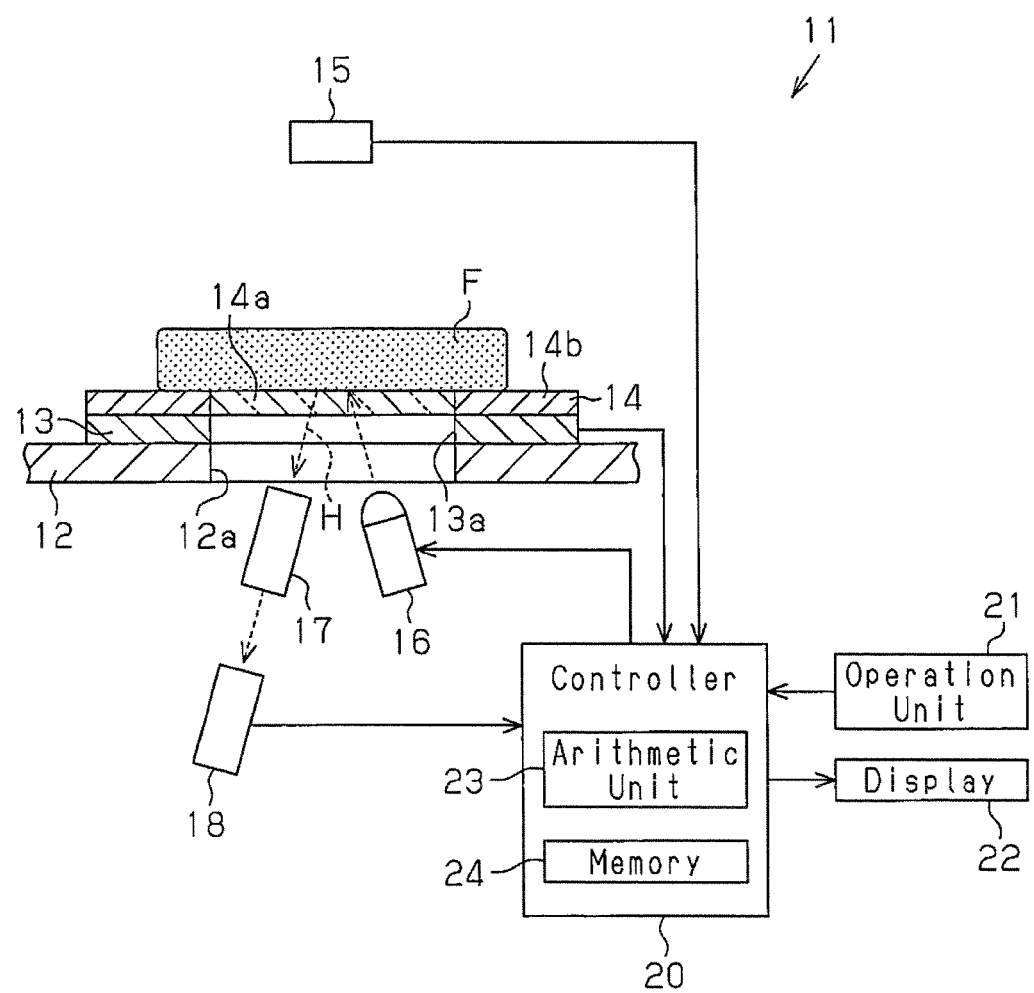
FIG. 1 is a schematic diagram showing a general structure of one embodiment of an analysis apparatus according to the present invention.

As shown in FIG. 1, an analysis apparatus 11 includes a flat seat 12 having a through hole 12a. The analysis apparatus 11 is capable of analyzing (estimating) protein, fat, and carbohydrate, which are three major nutrients (components) of food F. The food F is an example of an analyzed subject. The analysis apparatus 11 further includes a discoid weight sensor 13 located on the seat 12 and having a through hole 13a in a central portion. The weight sensor 13 is an example of a weight meter.

The through hole 12a of the seat 12 and the through hole 13a of the weight sensor 13 have the same size and are located to be aligned with each other as viewed from a direction perpendicular to a surface of the seat 12. The analysis apparatus 11 further includes a plate located on the weight sensor 13. An analyzed subject is placed on the plate. The food F is an example of the analyzed subject. The plate is, for example, a circular saucer 14, although not limited to the saucer 14. The weight sensor 13 measures the weight of the food F placed on the saucer 14.

Figure 2:
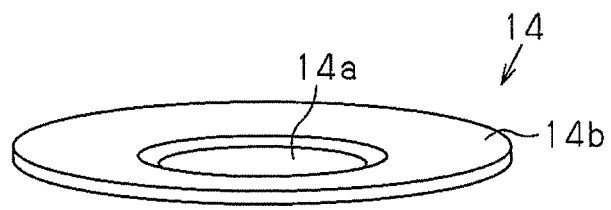
FIG. 2 is a perspective view showing a saucer of the analysis apparatus of FIG. 1.

As shown in FIGS. 1 and 2, a central circular portion of the saucer 14 is slightly recessed. The central portion of the saucer 14 is a light transmitting portion 14a, which transmits light. A portion excluding the light transmitting portion 14a is a light non-transmitting portion 14b, which transmits no light. In the present embodiment, the light transmitting portion 14a is formed from quartz glass, and the light non-transmitting portion 14b is formed from a melamine resin.

The light transmitting portion 14a of the saucer 14 and each through hole 12a, 13a have the same size and are located to be aligned with each other as viewed from the direction perpendicular to the surface of the seat 12. A temperature sensor 15 is located above the saucer 14. The temperature sensor 15 is an example of a temperature meter that measures the temperature of the food F placed on the saucer 14 in a non-contacting manner.

As shown in FIG. 1, a light emitter 16 is located below the seat 12. The light emitter 16 irradiates the food F placed on the saucer 14 with light (near-infrared light in the present embodiment) through the through hole 12a, the through hole 13a, and the light transmitting portion 14a. More specifically, the light emitter 16 irradiates the food F placed on the saucer 14 with light passing through the light transmitting portion 14a.

Additionally, a spectral unit 17 is located below the seat 12 and adjacent to the light emitter 16. When the light emitter 16 irradiates the food F with light, first reflection light H is reflected through the light transmitting portion 14a. The spectral unit 17 disperses the first reflection light H. The first reflection light H includes light of various wavelengths.

Figure 3:
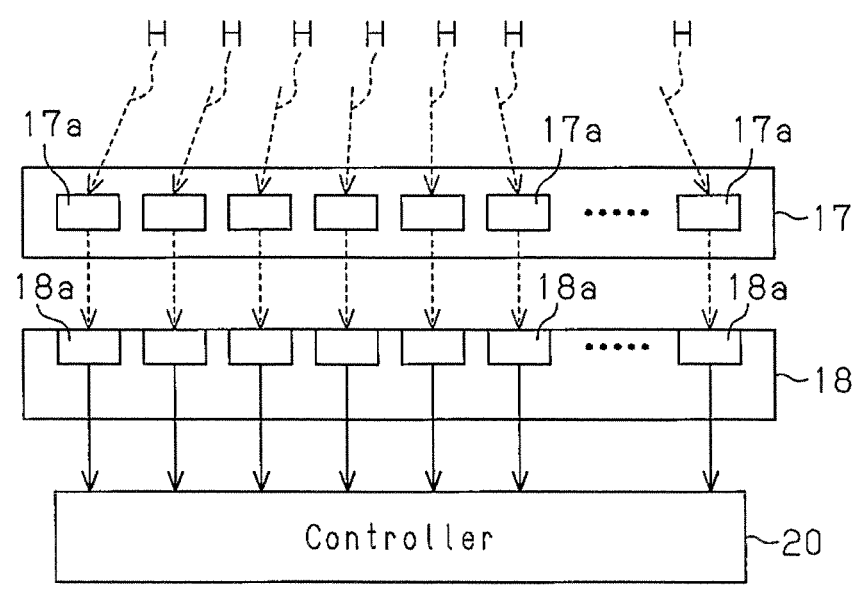
FIG. 3 is a schematic diagram showing a state when the analysis apparatus of FIG. 1 analyzes reflection light.

As shown in FIG. 3, the spectral unit 17 includes a plurality of optical filters 17a that allow transmission of light having a specified wavelength and restricts transmission of light having wavelengths excluding the specified wavelength. The optical filters 17a are regularly arranged. The optical filters 17a allow transmission of light having a wavelength that differs from one another. Thus, the optical filters 17a of the spectral unit 17 each disperse the first reflection light H into light having the corresponding specified wavelength. The dispersed light includes information of a single wavelength or a wavelength range having a predetermined width.

As shown in FIGS. 1 and 3, a light detector 18, which detects the first reflection light H that has been dispersed by the spectral unit 17, is located below the spectral unit 17. The light detector 18 includes a plurality of light reception elements 18a, which receive the first reflection light H passing through the optical filters 17a of the spectral unit 17, respectively. The light reception elements 18a are regularly arranged to correspond to the optical filters 17a, respectively.

More specifically, each light reception element 18a receives the first reflection light H passing through the corresponding optical filter 17a. In this case, it is preferred that each light reception element 18a has a satisfactory sensitivity to light that includes the information of the wavelength passing through the corresponding optical filter 17a. The light detector 18 converts light received by each light reception element 18a to an electric signal and transmits the electric signal to a controller 20, which will be described later, as detection data indicated in a voltage value corresponding to the amount of the received light.

As shown in FIG. 1, the analysis apparatus 11 includes the controller 20, which is an example of an analyzer that controls an operational state of the analysis apparatus 11, an operation unit 21, with which a user performs various operations, and a display 22, which shows an analysis result of a component of the food F or the like. The controller 20 is electrically connected to each of the weight sensor 13, the temperature sensor 15, the light emitter 16, the light detector 18, the operation unit 21, and the display 22.

The controller 20 also includes an arithmetic unit 23, which performs various arithmetic operations, and a memory 24. The memory 24 stores various control programs, detection data generated by the light detector 18, a regression equation, which will be described later, and the like. The controller 20 controls the light emitter 16 to emit light based on a signal transmitted from the operation unit 21 and analyzes (estimates) components contained in the food F based on the detection data transmitted from the light detector 18, signals transmitted from the weight sensor 13 and the temperature sensor 15, and the regression equation. Then, the controller 20 shows an analysis result (estimation result) of the components contained in the food F on the display 22.

The process for calculating the regression equation, which is used to analyze (estimate) components (protein, fat, and carbohydrate) contained in the food F, will now be described.

As shown in FIGS. 1 and 3, when calculating the regression equation, a food sample (analysis sample) containing components (protein, fat, and carbohydrate), the weight of which are each known, is placed on the saucer 14. The light emitter 16 irradiates the food sample with light (near-infrared light in the embodiment). The optical filters 17a of the spectral unit 17 each disperse second reflection light, which is reflected from the food sample, into light having the corresponding specified wavelength.

The second reflection light passing through each optical filter 17a is received by the corresponding light reception element 18a and converted to an electric signal. The memory 24 of the controller 20 stores the electric signal as detection data indicated in a voltage value corresponding to the amount of the received light. The detection data on the food F (analyzed subject) may be referred to as first detection data. The detection data on a food sample (analysis sample) may be referred to as second detection data.

When the number of the optical filters 17a the spectral unit 17 has is n, and the number of the light reception element 18a the light detector 18 has is n, an equation that obtains the protein weight $S_1$ is expressed as equation 1 shown below.

$$S_1 = T \cdot G \cdot (A_1 V_1 + A_2 V_2 + A_3 V_3 + \ldots + A_n V_n) \quad \text{equation 1}$$

In the same manner, an equation that obtains the fat weight $S_2$ is expressed as equation 2 shown below.

$$S_2 = T \cdot G \cdot (B_1 V_1 + B_2 V_2 + B_3 V_3 + \ldots + B_n V_n) \quad \text{equation 2}$$

In the same manner, an equation that obtains the carbohydrate weight $S_3$ is expressed as equation 3 shown below.

$$S_3 = T \cdot G \cdot (C_1 V_1 + C_2 V_2 + C_3 V_3 + \ldots + C_n V_n) \quad \text{equation 3}$$

In equations 1 to 3, T, G, $A_1$ to $A_n$, $B_1$ to $B_n$, $C_1$ to $C_n$, and $V_1$ to $V_n$ respectively denote the temperature of a food sample, the weight of the food sample, coefficients of protein, coefficients of fat, coefficients of carbohydrate, and voltage values (detection data). The voltage values (detection data) include information of a single wavelength or a wavelength range having a predetermined width. The voltage values and the design specification of the optical filters 17a would be used to calculate the near-infrared absorption spectrum of each wavelength in a measurement range of wavelengths. However, an arithmetic operation of reconfiguration to spectrum is necessary to calculate the near-infrared absorption spectrum. Here, instead of calculating the near-infrared absorption spectrum, the voltage values (detection data) are directly used.

When measuring the food sample, the parameters of T, G, $S_1$ to $S_3$, and $V_1$ to $V_n$ (second detection data) are known. Thus, the coefficients of protein $A_1$ to $A_n$, the coefficients of fat $B_1$ to $B_n$, and the coefficients of carbohydrate $C_1$ to $C_n$ may be calculated in accordance with equations 1 to 3 using a known statistical means. In this case, the known statistical means may be a chemometrics means, such as multiple regression analysis, principal component regression analysis, or PLS regression analysis.

When the coefficients of protein $A_1$ to $A_n$, which are obtained in the above manner, are assigned into equation 1, a first regression equation is obtained. The first regression equation calculates the protein weight $S_1$ contained in the food F. When the coefficients of fat $B_1$ to $B_n$, which are obtained in the above manner, are assigned into equation 2, a second regression equation is obtained. The second regression equation calculates the fat weight $S_2$ contained in the food F. When the coefficients of carbohydrate $C_1$ to $C_n$, which are obtained in the above manner, are assigned into equation 3, a third regression equation is obtained. The third regression equation calculates the carbohydrate weight $S_3$ contained in the food F. The first to third regression equations are stored in the memory 24 of the controller 20.

The operation of the analysis apparatus 11 will now be described when analyzing (estimating) the weight of each component (protein, fat, and carbohydrate) contained in the food F.

When analyzing the weight of each component (protein, fat, and carbohydrate) contained in the food F, firstly, the food F is placed on the saucer 14. When a user operates the operation unit 21, the light emitter 16 irradiates the food F with light (near-infrared light in the present embodiment). The optical filters 17a of the spectral unit 17 each disperse the first reflection light, which is reflected from the food F, into light having the corresponding specified wavelength.

Each light reception element 18a of the light detector 18 receives the dispersed light (first reflection light) passing through the corresponding optical filter 17a. The light received by each light reception element 18a is converted to an electric signal including the first detection data that is indicated in a voltage value corresponding to the amount of the light received by the light reception element 18a. The memory 24 of the controller 20 stores the first detection data. The arithmetic unit 23 of the controller 20 assigns the first detection data (voltage values: $V_1$ to $V_n$), the temperature of the food F (T), and the weight of the food F (G) into each of the first to third regression equations. This calculates the protein weight $S_1$, the fat weight $S_2$, and the carbohydrate weight $S_3$.

In this manner, the weight of each component (protein, fat, and carbohydrate) of the food F is analyzed (estimated). Subsequently, the controller 20 shows the analysis (estimation) result of the weight of the components (protein, fat, and carbohydrate) of the food F on the display 22.

The present embodiment has the advantages described below.

(1) The analysis apparatus 11 uses a post-processing spectroscopic technique, which does not need a spectral unit, such as a light chopper. Also, the analysis apparatus 11 analyzes (estimates) the weight of the components (protein, fat, and carbohydrate) contained in the food F without measuring the near-infrared absorption spectrum. This allows a brief and easy analysis of the weight of the components (protein, fat, and carbohydrate) contained in food F without enlarging the apparatus.

(2) The first to third regression equations, which are used to analyze the components contained in the food F, include T, which is the parameter of the temperature of the food F measured by the temperature sensor 15. Thus, the components contained in the food F are corrected based on the temperature of the food F measured by the temperature sensor 15. This increases the accuracy for analyzing the components contained in the food F.

(3) The first to third regression equations, which are used to analyze the components contained in the food F, include G, which is the parameter of the weight of the food F measured by the weight sensor 13. Thus, the weight of the components contained in the food F can be accurately analyzed (estimated) based on the weight of the food F measured by the weight sensor 13.

(4) The analysis apparatus 11 analyzes the components of the food F by irradiating the food F placed on the saucer 14 having the light transmitting portion 14a with light from a lower side of the saucer 14. Thus, even when water vapor or the like is generated due to the heated food F, the light emitter 16 and the light detector 18 will not be misted with such water vapor. This limits decreases in the accuracy for analyzing the components of the food F caused by generation of water vapor or the like. Additionally, the food F is located on the saucer 14 during the analysis of the components of the food F. Thus, the components may be easily analyzed even when the food F is liquid such as curry.

Modified Examples

The embodiment may be modified as follows.

Figure 4:
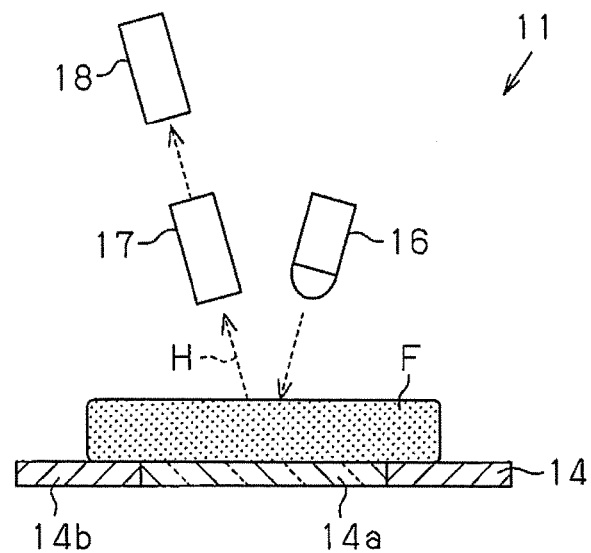
FIG. 4 is a schematic diagram showing a situation of a modified example when food placed on the saucer is irradiated with light from above, and the reflection light is dispersed.

As shown in FIG. 4, the analysis apparatus 11 may include the light emitter 16, the spectral unit 17, and the light detector 18 that are located above the food F placed on the saucer 14. In this case, the saucer 14 may be entirely formed from a light blocking material.

Figure 5:
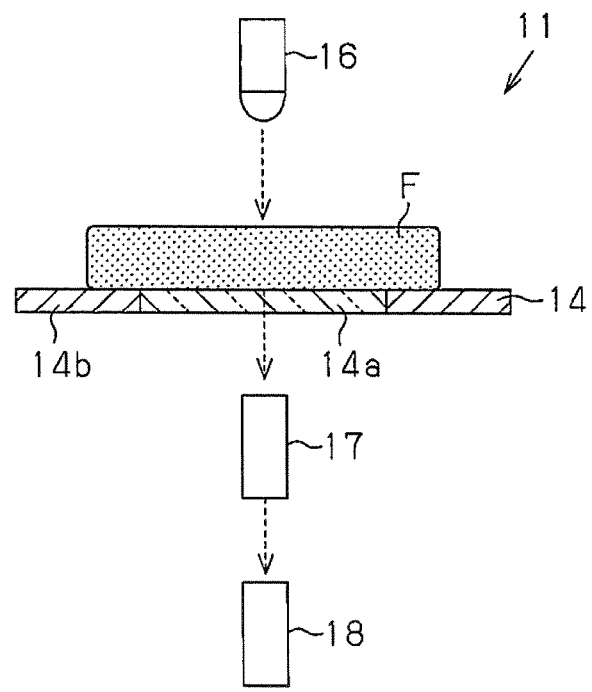
FIG. 5 is a schematic diagram showing a situation of a modified example when food placed on the saucer is irradiated with light from above, and the transmission light is dispersed.

As shown in FIG. 5, in the analysis apparatus 11, the light emitter 16 may be located above the food F placed on the saucer 14 when the spectral unit 17 and the light detector 18 are located below the saucer 14. In this case, when the light emitter 16 irradiates the food F with light, first transmission light, which passes through the food F and the light transmitting portion 14a of the saucer 14, is dispersed by the spectral unit 17 and detected by the light detector 18. In this case, when the light emitter 16 emits light to the food sample, each component weight of which is known in advance, and second transmission light passes through the food sample and the light transmitting portion 14a of the saucer 14. The second transmission light is used to calculate the first to third regression equations, instead of the second reflection light.

The first to third regression equations do not have to include T. That is, when estimating the components (protein, fat, and carbohydrate) contained in the food F, the components need not be corrected by the temperature of the food F.

The first to third regression equations do not have to include G. That is, when estimating the components (protein, fat, and carbohydrate) contained in the food F, the weight of the components is not necessarily estimated.

The first to third regression equations do not have to include T nor G. More specifically, the components (protein, fat, and carbohydrate) contained in the food F may be estimated without using the temperature of the food F to correct the components and without estimating the weight of the components. In other words, the components (protein, fat, and carbohydrate) contained in the food F may only be estimated.

The analysis apparatus 11 may be used to analyze (estimate) calories of the food F. In this case, a regression equation that estimates the calories of the food F is calculated using food, the calories of which are known in advance, as an analysis sample. The regression equation is stored in the memory 24. This is the same manner as the above embodiment, which analyzes (estimates) the components (protein, fat, and carbohydrate) of the food F. An equation that obtains calories K of the food F is expressed as equation 4 shown below.

$$K_2 = T \cdot G \cdot (D_1 V_1 + D_2 V_2 + D_3 V_3 + \ldots + D_n V_n) \quad \text{equation 4}$$

In this case, $D_1$ to $D_n$ are coefficients of calories, which are obtained using the same process as, for example, the coefficients of protein $A_1$ to $A_n$ of the above embodiment. When the coefficients of calories $D_1$ to $D_n$ are obtained as described above and assigned into equation 4, a fourth regression equation is obtained. The fourth regression equation is used to calculate the calories K of the food F. The arithmetic unit 23 calculates the calories K of the food F by assigning the detection data (first detection data) of the food F (voltage values; $V_1$ to $V_n$), the temperature of the food F (T), and the weight of the food F (G) into the fourth regression equation. In this manner, the calories of the food F are analyzed (estimated). This allows a brief and easy estimation of the calories of the food F without enlarging the apparatus. Alternatively, after estimating the components (protein, fat, and carbohydrate) contained in the food F, the components may each be multiplied by the coefficients of calories and added together. This obtains the calories K of the food F.

When the food F contains an inner component that significantly differs from an outer component (e.g., tempura or cabbage roll), the components may be analyzed after mincing the food F. This allows an accurate component analysis even when the food F contains an inner component that significantly differs from an outer component.

When the detection data obtained by the light detector 18 accurately correlates with components of an analyzed subject, the light emitter 16 may irradiates the analyzed subject with light having a wavelength range other than near-infrared light.

The analysis apparatus 11 may analyze a component of soil, a chemical, or the like, as an analyzed subject.

The invention claimed is:

1. An analysis apparatus capable of analyzing a component contained in an analyzed subject or calories of the analyzed subject, the analysis apparatus comprising:
   a light emitter that emits light;
   a spectral unit that is configured to disperse first reflection light reflected from the analyzed subject or first transmission light transmitted through the analyzed subject when the light emitter irradiates the analyzed subject with light;
   a light detector that detects the first reflection light or the first transmission light dispersed by the spectral unit and generates first detection data that is a voltage value corresponding to an amount of received light, wherein, when the light emitter irradiates an analysis sample with light, in which the analysis sample includes a known component or has known calories, the light detector detects second reflection light, which is reflected from the analysis sample and dispersed by the spectral unit, or second transmission light, which is transmitted through the analysis sample and is dispersed by the spectral unit, and generates second detection data that is a voltage value corresponding to an amount of received light;
   a memory that stores a regression equation calculated directly using the second detection data as a parameter; and
   an analyzer that estimates the component contained in the analyzed subject or the calories of the analyzed subject directly using the first detection data and the regression equation stored in the memory.

2. The analysis apparatus according to claim 1, further comprising a temperature meter capable of measuring temperature of the analyzed subject,
   wherein the analyzer corrects the component contained in the analyzed subject or the calories of the analyzed subject based on the temperature of the analyzed subject measured by the temperature meter.

3. The analysis apparatus according to claim 1, further comprising a weight meter capable of measuring weight of the analyzed subject,
   wherein the regression equation stored in the memory is calculated using the second detection data and the weight of the analysis sample measured by the weight meter as parameters, and
   the analyzer estimates weight of the component contained in the analyzed subject using the first detection data, the weight of the analyzed subject measured by the weight meter, and the regression equation.

4. The analysis apparatus according to claim 1, further comprising a light transmissive plate on which the analyzed subject is placed, wherein the light emitter, the spectral unit, and the light detector are located below the plate, the light emitter irradiates the analyzed subject placed on the plate with light passing through the plate, the spectral unit disperses first reflection light reflected from the analyzed subject through the plate, and the light detector detects the first reflection light dispersed by the spectral unit.

5. The analysis apparatus according to claim 1, wherein the analyzed subject is food, and the component is at least one of protein, fat, and carbohydrate.

6. The analysis apparatus according to claim 1, wherein the spectral unit includes a plurality of optical filters, each of the optical filters allows transmission of light having a specified wavelength and restricts transmission of light having wavelengths other than the specified wavelength, the light detector includes a plurality of light reception elements, and each of the light reception elements receives light transmitted through a corresponding one of the optical filters.

\* \* \* \* \*